US00PP30208P2

(12) United States Plant Patent
Cunill

(10) Patent No.: US PP30,208 P2
(45) Date of Patent: Feb. 19, 2019

(54) OLIVE TREE NAMED 'LECCIANA'

(50) Latin Name: *Olea europaea*
Varietal Denomination: Lecciana

(71) Applicant: Agromillora California, Gridley, CA (US)

(72) Inventor: Marisa Cunill, Barcelona (ES)

(73) Assignee: Agromillora California, Gridley, CA (US)

( * ) Notice: Subject to any disclaimer, the term of this patent is extended or adjusted under 35 U.S.C. 154(b) by 0 days.

(21) Appl. No.: 15/732,215

(22) Filed: Oct. 4, 2017

(51) Int. Cl.
*A01H 5/08* (2018.01)

(52) U.S. Cl.
USPC ..... Plt./158
CPC ..... *A01H 5/08* (2013.01)

(58) Field of Classification Search
USPC ..... Plt./158
CPC ..... A01H 5/08; A01H 5/00
See application file for complete search history.

*Primary Examiner* — Kent L Bell
(74) *Attorney, Agent, or Firm* — Samuel R. McCoy, Jr.

(57) ABSTRACT

A new and distinct cultivar of *Olea* plant named 'Lecciana', used primarily for oil production, which is characterized by the combination of a compact growth habit, uniform and continuous fruit production, high polyphenol content, and the stability of these characteristics from generation to generation.

7 Drawing Sheets

Latin name of the genus and species: The Latin name of the genus and species of the novel variety disclosed herein is *Olea europaea.*

Variety denomination: The inventive cultivar of *Olea* disclosed herein has been given the variety denomination 'Lecciana'.

BACKGROUND OF THE INVENTION

Parentage: The claimed plant was created in Barcelona, Spain in 1998 as a result of a planned breeding program. The purpose of the breeding program was to develop a low vigor variety with a suitable tree structure, adapted to a high-density production system. The claimed plant is the result of a cross between *Olea europaea* 'Arbosana OLINT' (U.S. Plant Pat. No. 18,598), the seed parent, and *Olea europaea* 'Leccino' (not patented), the pollen parent. The claimed plant was finally selected in 2016 and was given the name 'Lecciana'. The new variety exhibits high productivity and precocity. Among other important traits, olive fruits are retained after reaching maturity allowing optimum mechanical harvesting with minimum loss.

Asexual Reproduction: Asexual reproduction of 'Lecciana', by way of rooting semi-ligneous stem cuttings, was first performed during the summer of 2002 in Bari, Italy. Through 14 subsequent generations, the unique features of this cultivar have proven to be stable and true to type.

SUMMARY OF THE INVENTION

The cultivar 'Lecciana' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Lecciana'. These characteristics in combination distinguish 'Lecciana' as a new and distinct *Olea europaea* cultivar:

1. *Olea* 'Lecciana' exhibits a compact growth habit which requires less pruning, making it suitable to growing in a hedgerow for high density production; and
2. *Olea* 'Lecciana' exhibits less damage to stems and branches as a result of mechanical harvesting; and
3. *Olea* 'Lecciana' exhibits improved cold hardiness; and
4. *Olea* 'Lecciana' exhibits precocious fruiting and a high fruit yield; and
5. *Olea* 'Lecciana' exhibits high pulp consistency which reduces damage from mechanical harvesting; and
6. *Olea* 'Lecciana' exhibits fruit which is retained after reaching maturity allowing optimum mechanical harvesting with minimum loss.

BRIEF DESCRIPTION OF THE FIGURES

The accompanying photographic drawings illustrate 'Lecciana' with the color being as nearly true as is possible with color illustrations of this type.

BOTANICAL DESCRIPTION OF THE PLANT

Figure 1:
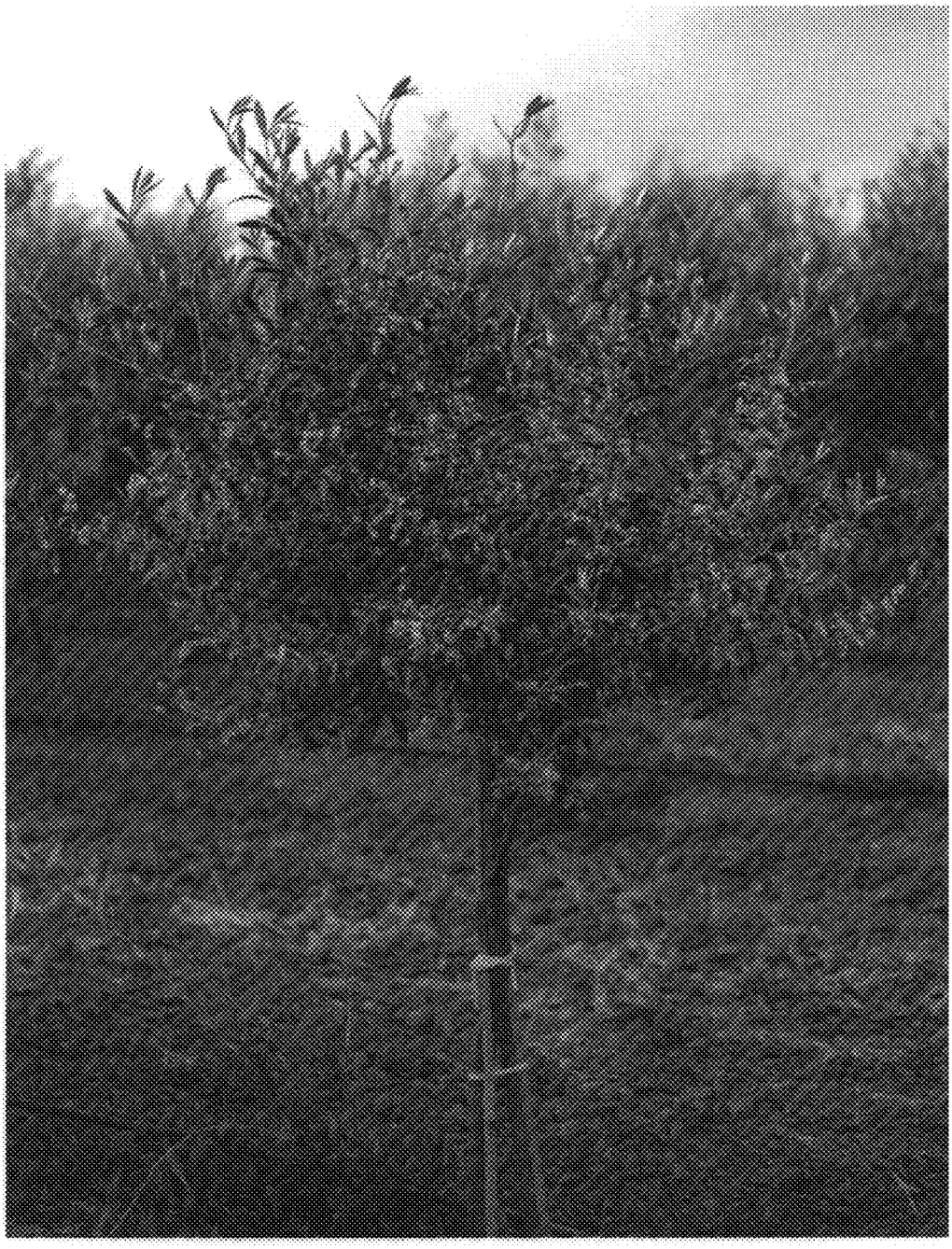
FIG. 1 shows an exemplary 3 year old 'Lecciana' tree during flowering.
Figure 2:
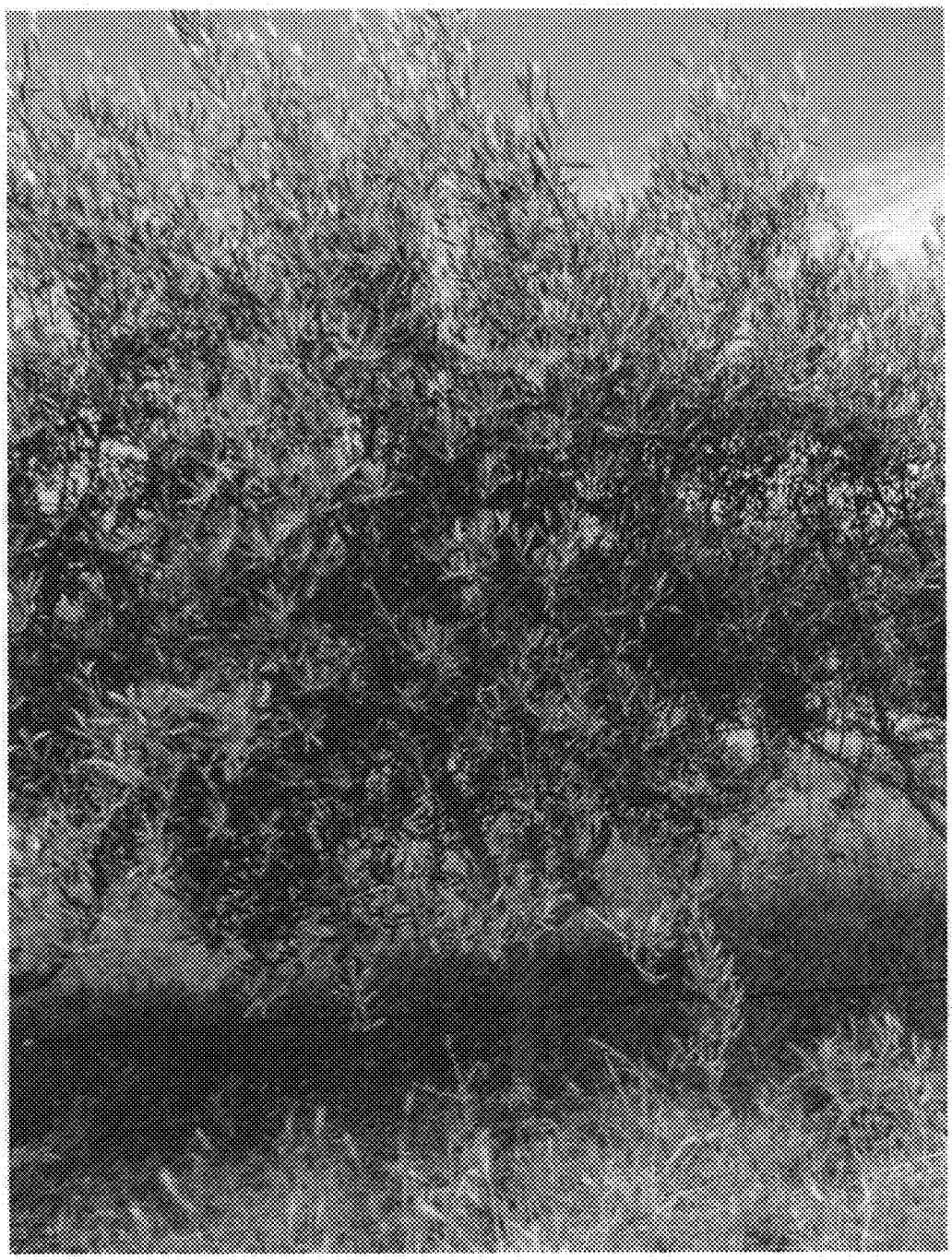
FIG. 2 shows an exemplary 6 year old 'Lecciana' tree.
Figure 3:
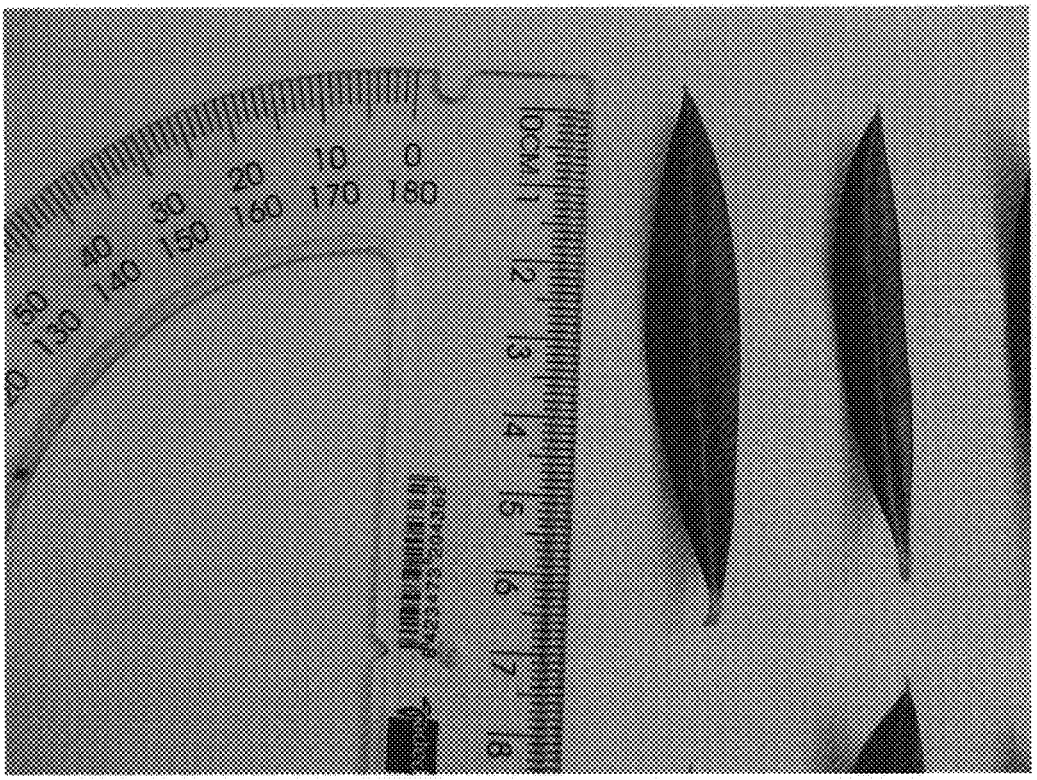
FIG. 3 shows the leaves of 'Lecciana'.
Figure 4:
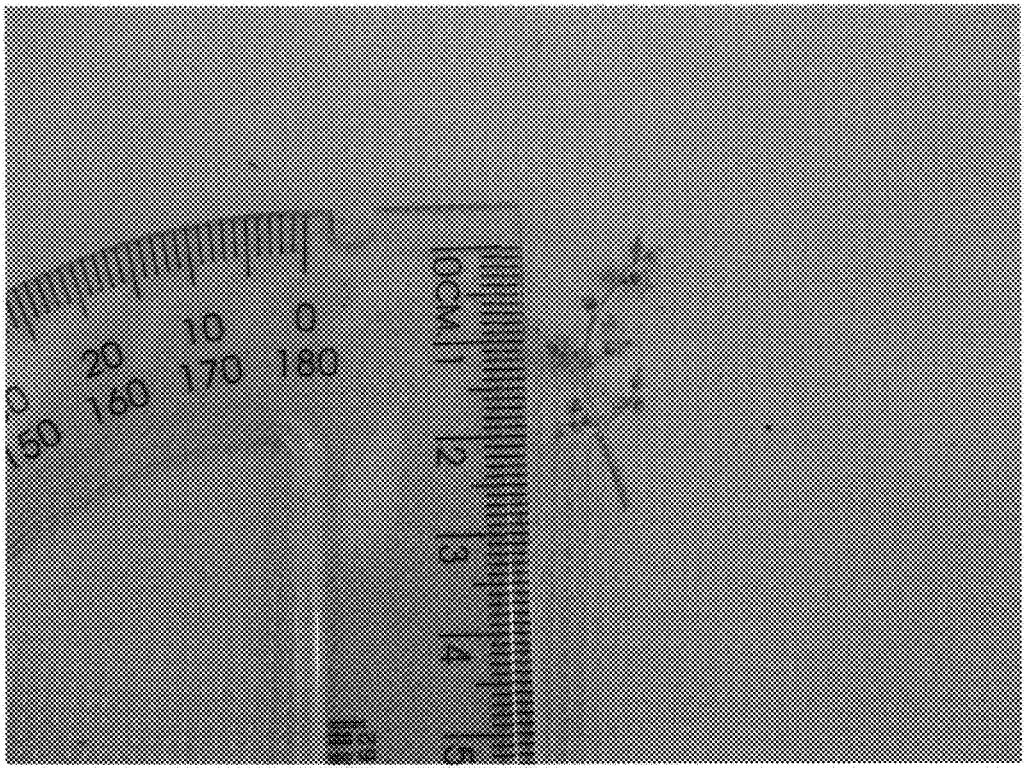
FIG. 4 shows the flowers of 'Lecciana'.
Figure 5:
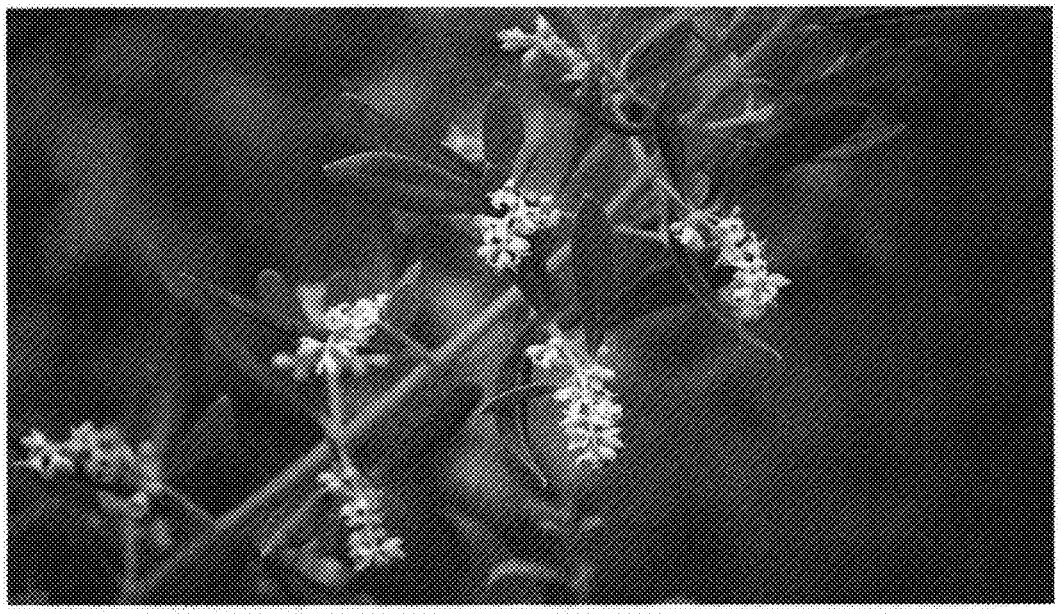
FIG. 5 shows flowers on the tree of 'Lecciana'.
Figure 6:
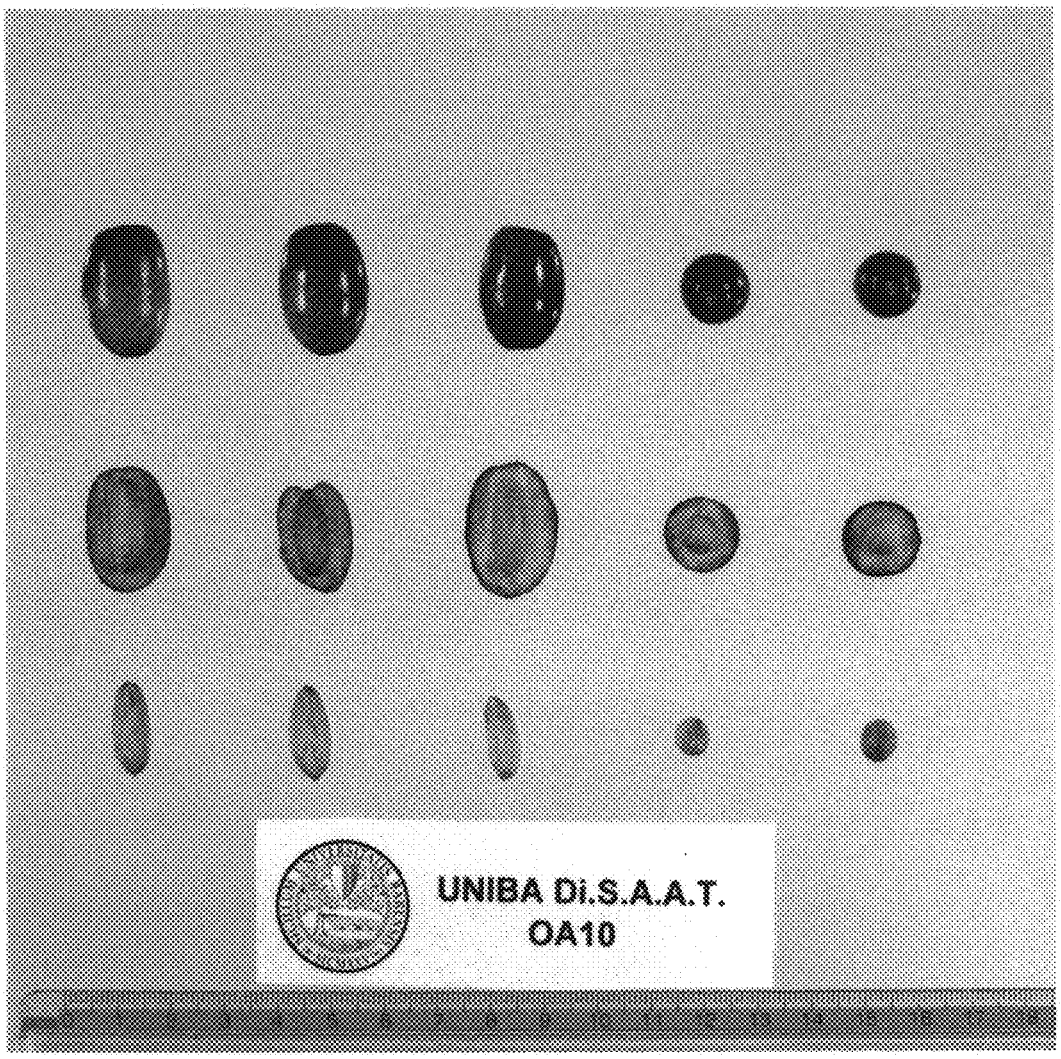
FIG. 6 shows whole and cut fruits of 'Lecciana', as well as stones.
Figure 7:
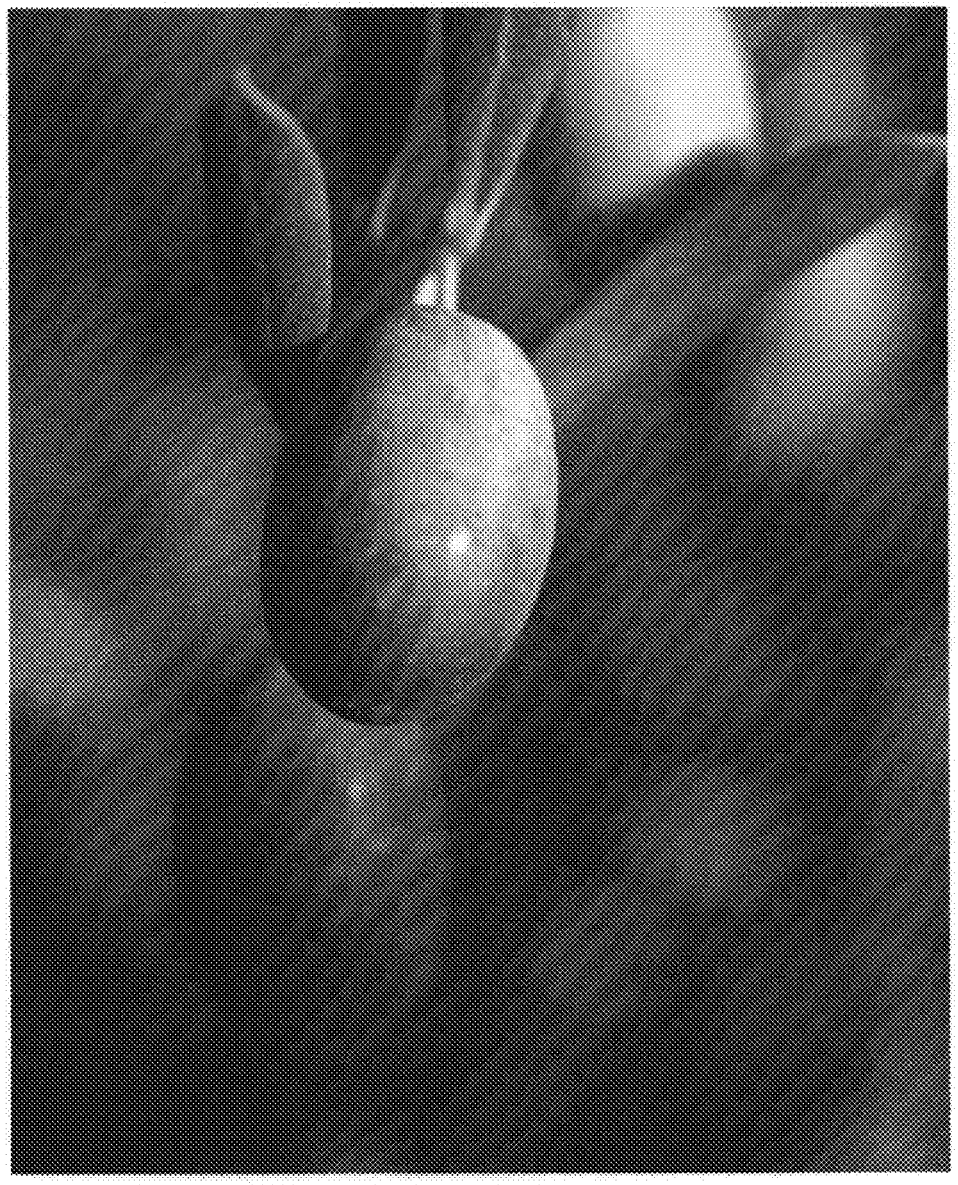
FIG. 7 shows the fruit of 'Lecciana'.

The following detailed description sets forth the characteristics of 'Lecciana'. The data which defines these characteristics was collected in May of 2017 under natural daylight on plants produced by semi-ligneous cuttings carried out in Gridley, Calif. in the Sacramento Valley. The plants were grown under normal field conditions with drip irrigation. The age of the observed plant was 4 years.

Those skilled in the art will appreciate that certain characteristics will vary with older or, conversely, with younger plants. 'Lecciana' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color designations are presented with reference to the "Dictionary of Color" by A. Maerz and M. Rea Paul, Second Edition (1950).

A botanical description of 'Lecciana' and comparisons with the parent plants and most similar commercial *Olea* cultivar known to the inventor are provided below.

Tree:

*Growth habit*.—Evergreen tree.

*Plant form*.—Globular.

*Average height from base to top of foliage*.—Approximately 244 to 274 cm.

*Average width*.—Approximately 76 to 91 cm.

*Plant vigor*.—Medium low.

*Propagation details*.—Asexual propagation is accomplished by rooting semi-ligneous stem cuttings.

*Time to produce a fruit bearing tree*.—3 years.

*Chilling requirements*.—Similar to that of other *Olea europaea* varieties.

*Productivity*.—Production level is uniform, with very good distribution through the branches, and good oil production.

*Regularity of bearing fruit*.—Regular.

*Disease and pest resistance or susceptibility*.—Sensitivity to olive fruit fly (*Bactrocera oleae*) is medium to low. Otherwise, plants have not been observed to be notably susceptible or resistant to pathogens and pests common to *Olea europaea*.

*Environmental tolerances*.—USDA Hardiness Zones 8 through 10; exhibits good resistance to low temperatures.

Root system:

*Rooting habit*.—Dense, freely branching fibrous roots.

*Distribution in the soil profile*.—Shallow to moderately deep.

*Texture*.—Smooth; glabrous.

*Color, juvenile roots*.—Mastic (13-E-5).

*Color, older roots*.—Meadowlark (15-E-7).

Stems:

*Branching habit*.—Central trunk gives rise to a plurality of main stems, themselves freely branching, and bearing numerous lateral branches.

*Trunk*.—Size — 13 cm circumference at 33 cm above the soil surface. Surface texture — Smooth. Color code — Wild Iris (44-B-5).

*Main stems*.—Quantity — 3 to 5, depending on pruning practices. Aspect — Upright and outward. Stem strength — Flexible and strong. Cross-section — Rounded. Size — Small; 8 cm circumference at approximately 3 years of age. Surface texture, juvenile stems — Smooth. Surface texture, mature stems — Smooth with raised lenticels. Color, juvenile — Light Grey (36-A-1). Color, mature (one year and older) — Dusty Green (22-C-1). Lenticels — Abundant; 0.9 mm long and 0.4 mm wide; color is Prairie (13-F-6). Internode length — Ranging from 3.0 to 10 cm.

*Lateral branches*.—Abundance of lateral branches — Very abundant; several hundred. Cross-section — Round. Length — Ranging from 1.0 to 2.0 meters. Diameter — 1.0 cm. Internode length on lateral branches — 1.0 to 3.0 cm. Texture — Smooth with raised lenticels. Aspect — Outward. Strength — Flexible and strong. Color, juvenile — (21-1-3). Color, mature — Cerro Green (22-L-5). Pubescence — Glabrous.

Foliage:

*Arrangement*.—Opposite.

*Attachment*.—Petiolate.

*Division*.—Simple.

*Lamina*.—Dimensions — 58 to 70 mm long and 8.5 to 11.5 mm wide. Thickness — 1.5 to 2.0 mm. Shape — Elliptic to nearly symmetrical. Aspect — Varying from slightly curled downward to slightly curled upward. Apex — Acute. Base — Cuneate. Margin — Entire; not undulated. Texture of adaxial surface — Smooth. Texture of abaxial surface — Slightly pubescent. Color — Juvenile foliage, adaxial surface — (22-L-8). Juvenile foliage, abaxial surface — (19-D-5). Mature foliage, adaxial surface — Chrome Green (22-L-12). Mature foliage, abaxial surface — Chrysolite Green (19-K-3). Venation — Pattern — Pinnate. Color, adaxial surface — (14-C-1). Color, abaxial surface — (20-G-3). Thickness — 1.0 mm.

*Petiole*.—Length — 2.0 mm. Diameter — 1.0 mm. Texture — Smooth. Strength — Medium. Color — (12-1-1).

Inflorescence:

*Type*.—Panicle.

*Natural flowering season*.—Early May in Gridley, California.

*Flowering habit*.—Flowering once per year.

*Inflorescence dimensions*.—Ranging from 3.0 to 6.0 cm long and 1.5 to 2.5 cm wide.

*Inflorescence abundance*.—Abundant.

*Quantity of florets per inflorescence*.—11 to 16.

*Peduncle*.—Dimensions — 3.0 to 6.0 cm long and 1.5 mm in diameter. Texture — Smooth. Strength — Medium. Color — Turtle Green (19-G-4).

*Pedicels*.—Dimensions — 1.0 to 4.0 mm long and 1.0 mm in diameter. Texture — Smooth. Strength — Medium. Color — Reed Green (19-D-2).

Flower buds:

*Bud shape*.—Globular.

*Bud dimensions*.—2.5 to 4.0 mm long and 2.0 mm in diameter.

*Bud color*.—(18-B-2).

Flower:

*Flower type*.—Perfect; simple.

*Flower shape*.—Cruciform.

*Persistence*.—Not persistent.

*Flower aspect*.—Erect to horizontal.

*Fragrance*.—Very mild fragrance.

*Dimensions*.—Approximately 3.0 to 6.0 mm in diameter and 2.0 to 3.0 mm tall.

*Calyx*.—Quantity of sepals — 4. Arrangement — Rotate; sepals arranged in a single whorl. Diameter of calyx — 1.0 cm. Sepals — Fused or unfused — Fused. Sepal dimensions — 1.0 mm long and 1.0 mm wide. Shape — Bell shaped. Apex — Obtuse. Base — Cuneate. Margin — Entire. Texture — Smooth. Color (upper side) — (18-A-1). Color (under side) — (18-A-1).

*Petals*.—Arrangement — Rotate; petals arranged in a single whorl. Quantity — 4. Fused or unfused — Sympetalous; petals fused at the proximal half of the corolla. Dimensions of the free portion of petals — 2.0 mm. Shape — Acute. Apex — Acute. Base — Cuneate. Margin — Entire; not undulated. Texture — Smooth. Color when opening (upper side) — White (1-A-1). Color when opening (under side) — White (1-A-1). Color when fully opened (upper side) — White (1-A-1). Color when fully opened (under side) — White (1-A-1). Color fading to — Not fading.

Reproductive organs:

*Androecium*.—Stamen quantity — Two. Filament — Dimensions — Approximately 0.75 mm. Color — (17-D-1). Anther — Anther attachment — Basifixed. Anther shape — Hemispherical. Anther size — 1.0 mm. Anther color — (17-L-1). Pollen — Abundance of pollen — Abundant. Pollen color — Empire Yellow (9-K-3).

*Gynoecium*.—Pistil quantity — One. Stigma — Shape — Bifid cone shape. Dimensions — Approximately 0.75 mm. Color — Rivage Green (17-1-7). Style — Dimensions — Approximately 0.75 mm. Color — (17-D-4). Ovary — Position — Superior. Shape — Round. Diameter — Approximately 0.75 mm. Color — (18-K-11).

Seed and fruit:

*Fruit*.—Date of maturity — Mid October in Gridley, California. Size — Small. Weight — Approximately 3.5 grams. Diameter — 16 mm, on average. Length — 23 mm, on average. Form — Elliptical and slightly asymmetrical. Suture — None. Stem cavity — Small. Stem — 4.5 mm, on average. Caliper — Very small. Apex — Slightly rounded. Pistil point — Obscure. Skin — Thickness — Less than 1 mm. Texture — Smooth. Tendency to crack — None. Color — Ground color — Apple Green (19-J-6). Flesh color — Oyster Gray (19-A-2). Color of surface — Oyster Gray (19-A-2). Color of pit — Oyster Gray (19-A-2). Juice production — Oil production excellent. Flavor — Unique. Ripening — Even.

*Stone*.—Quantity — One. Shape — Elliptical, cross section is round. Type — Cling. Fibers — None. Weight — Small, less than 0.5 gram. Length — 15 mm. Width — 6 mm. Thickness — 6 mm. Apex — Pointed. Base — Ovate. Color (dry) — Grayish brown (46-D-3). Texture — Slightly grooved. Mucron — Obscure. Suture — Marked. Sides — About even. Ridges — Very faint and uneven. Tendency to split — None known. Use — Oil production. Harvesting — Mechanical harvesting, Mid October. Oil — The oil yield is approximately 15% when the skin of the fruit is mature. A chemical analysis of the oil is provided in Table 1 below:

TABLE 1

| | |
|---|---|
| Isomeric Diacylglycerols | 97.5% |
| Polyphenols (total, as tyrosol) | 330 mg/kg |
| Pyropheophytines | Less than 1%. |

COMPARISON WITH THE PARENT PLANTS

Plants of the new cultivar 'Lecciana' may be distinguished from the pollen parent, *Olea europaea* 'Arbosana OLINT' (U.S. Plant Pat. No. 18,598), by the characteristics described in Table 2.

TABLE 2

| Characteristic | 'Lecciana' | 'Arbosana OLINT' |
|---|---|---|
| Plant vigor. | Medium low. | Low. |
| Ability to withstand damage to fruit due to mechanical harvesting. | Very good. | Good. |
| Cold tolerance. | Cold tolerant. | Average tolerance to cold. |
| Resistance to olive knot disease. | Tolerant. | Average tolerance to olive knot disease. |
| Time of harvest. | Mid October. | Late October. |

Plants of the new cultivar 'Lecciana' may be distinguished from the seed parent, *Olea europaea* 'Leccino' (not patented), by the characteristics described in Table 3.

TABLE 3

| Characteristic | 'Lecciana' | 'Leccino' |
|---|---|---|
| Growth habit. | Compact tree, growing to approximately 244 to 274 cm tall. | Tall tree, growing to approximately 600 cm tall. |
| Vigor. | Medium low. | Vigorous. |
| Fruit size. | Small. | Medium. |

COMPARISON WITH THE CLOSEST KNOWN COMMERCIAL VARIETY

Plants of the new cultivar 'Lecciana' may be distinguished from the commercial variety, *Olea* 'Arbequina OLINT' (U.S. Plant Pat. No. 18,600), by the characteristics described in Table 4.

TABLE 4

| Characteristic | 'Lecciana' | 'Arbequina OLINT' |
|---|---|---|
| Vigor. | Medium low. | Medium. |
| Height of tree. | Approximately 244 to 274 cm tall. | Approximately 304 to 335 cm tall. |
| Time of harvest. | Mid October. | First week of October. |
| Ability to withstand damage to fruit due to mechanical harvesting. | Very good. | Good. |

That which is claimed is:

1. A new and distinct cultivar of *Olea* plant named 'Lecciana', substantially as described and illustrated herein.

* * * * *